US009856185B2

(12) United States Patent
Griffith Cruz et al.

(10) Patent No.: US 9,856,185 B2
(45) Date of Patent: Jan. 2, 2018

(54) MODULAR REFINING REACTOR AND REFINING METHODS

(71) Applicant: LytOil, Inc., Sunnyvale, CA (US)

(72) Inventors: Joe Griffith Cruz, San Jose, CA (US); Scott Ray Mobley, Portola Valley, CA (US); Philip David Fulmer, San Jose, CA (US)

(73) Assignee: LYTOIL, INC., Sunnyvale, CA (US)

( * ) Notice: Subject to any disclaimer, the term of this patent is extended or adjusted under 35 U.S.C. 154(b) by 350 days.

(21) Appl. No.: 14/515,196

(22) Filed: Oct. 15, 2014

(65) Prior Publication Data

US 2016/0107953 A1 Apr. 21, 2016

(51) Int. Cl.
*C07C 5/03* (2006.01)
*C07C 2/56* (2006.01)
(Continued)

(52) U.S. Cl.
CPC ................ *C07C 5/03* (2013.01); *B01J 10/00* (2013.01); *B01J 19/087* (2013.01); *B01J 19/088* (2013.01); *B01J 19/129* (2013.01); *B01J 19/24* (2013.01); *B01J 19/245* (2013.01); *C07C 2/56* (2013.01); *B01J 2219/0004* (2013.01); *B01J 2219/00065* (2013.01); *B01J 2219/00067* (2013.01); *B01J 2219/00094* (2013.01); *B01J 2219/00132* (2013.01); *B01J 2219/00135* (2013.01);
(Continued)

(58) Field of Classification Search
None
See application file for complete search history.

(56) References Cited

U.S. PATENT DOCUMENTS 4,149,853 A * 4/1979 DesMarais, Jr. .......... C10L 1/14 208/17
7,806,947 B2 10/2010 Gunnerman et al.
(Continued)

FOREIGN PATENT DOCUMENTS

CN 1360008 A 7/2002
CN 102942950 A 2/2013

OTHER PUBLICATIONS

International Search Report and Written Opinion dated Jan. 29, 2016 for PCT Application No. PCT/US2015/055765.

*Primary Examiner* — Kishor Mayekar
(74) *Attorney, Agent, or Firm* — Moser Taboada; Alan Taboada

(57) ABSTRACT

Methods and apparatus for refining feedstocks, such as crude or synthetic oil, and like feedstocks, are disclosed herein. In some embodiments, a reactor for refining a feedstock includes: a chamber having an inner volume to hold a liquid feedstock, a feedstock inlet port, a process gas inlet port, and an outlet port; a gas diffuser housed within the chamber and coupled to the process gas inlet port; and a radical generator coupled in fluid communication with the inner volume via the gas diffuser. In some embodiments, a method for refining feedstock includes: providing liquid feedstock to an inner volume of a reactor; flowing a radicalized process gas from a radical generator into the inner volume and into contact with the feedstock via a gas diffuser to fractionate the feedstock and produce one or more fractions of product in a vaporous mixture; and collecting a desired product from the vaporous mixture.

11 Claims, 4 Drawing Sheets

200
224
222
204
227
216
205
207
211
218
202
203
208
206
212
214
210
226
220

(51) Int. Cl.

| | |
|---|---|
| ***B01J 19/08*** | (2006.01) |
| ***B01J 19/12*** | (2006.01) |
| ***B01J 19/24*** | (2006.01) |
| ***B01J 10/00*** | (2006.01) |

(52) U.S. Cl.
CPC ................. *B01J 2219/00159* (2013.01); *B01J 2219/00173* (2013.01); *B01J 2219/0875* (2013.01); *B01J 2219/0894* (2013.01); *B01J 2219/0898* (2013.01); *B01J 2219/1203* (2013.01)

(56) References Cited

U.S. PATENT DOCUMENTS

| | | | | |
|---|---|---|---|---|
| 8,203,027 | B2 | 6/2012 | Gunnerman et al. | |
| 8,226,817 | B2 | 7/2012 | Gunnerman et al. | |
| 2002/0068017 | A1 * | 6/2002 | Naatz ..................... | G01N 21/71 422/80 |
| 2008/0179529 | A1 * | 7/2008 | Shock ................ | G01N 21/3504 250/343 |
| 2012/0297665 | A1 | 11/2012 | Goerz | |
| 2013/0126485 | A1 | 5/2013 | Foret | |
| 2014/0054504 | A1 | 2/2014 | Yoon et al. | |

* cited by examiner

MODULAR REFINING REACTOR AND REFINING METHODS

FIELD

Embodiments of the invention generally relate to apparatus and methods for refining oil-based feedstocks.

BACKGROUND

Oils are the most widely used sources for power generation in the world. Fuels and other products derived from crude oil offer a wide range of utility, i.e., from consumer uses such as fuels for engines and home heating to commercial and industrial uses such as fuels for boilers, furnaces, and power plants as well as specialty chemicals. Crude oils are a mixture of hydrocarbons differing widely in molecular weight, boiling and melting points, and reactivity, including light components and heavy components. Furthermore, components that are detrimental to the environment, such as sulfur compounds, naphthenes, and benzene-containing compounds, often remain in products obtained by refining processes.

Many processes have been developed to refine oils. Conventional refining processes include heating oils to very high temperatures and very high pressures. Considerable amounts of energy are required to heat oils in the refining process. And, apparatus capable of processing oils at high temperatures and pressures is expensive and relatively inefficient. Moreover, refining processes include the use of processing additives, such as catalysts, which typically consist of transition metals and/or aluminas, silicas, and/or zeolites, which are costly, are not recyclable, and must be replenished often.

Furthermore, oils and other oil-based materials, such as plastics, polymers, and other oil-based chemicals and products, are recycled in many municipalities. However, oils and oil-based products, which can be reclaimed as feedstocks, raises environmental concerns during transport and is commensurately expensive.

Therefore, the inventors have provided improved apparatus and methods to refine oils and other feedstocks.

SUMMARY

Methods and apparatus for refining feedstocks, such as crude or synthetic oil, and like feedstocks, are disclosed herein. In some embodiments, a reactor for refining a feedstock includes: a chamber having an inner volume to hold a liquid feedstock, a feedstock inlet port, a process gas inlet port, and an outlet port; a gas diffuser housed within the chamber and coupled to the process gas inlet port; and a radical generator coupled in fluid communication with the inner volume via the gas diffuser.

In some embodiments, a reactor for refining a feedstock includes: a chamber having an inner volume to hold a liquid feedstock, a feedstock inlet port, a process gas inlet port, and an outlet port; a gas distribution ring having a plurality of holes forming a perforated surface within the inner volume; a radical generator coupled in fluid communication with the inner volume via the gas distribution ring; a reformer having a plurality of filaments disposed downstream of the gas distribution ring; and a controller to control operation of the reactor and configured to communicate with a remote computer network.

In some embodiments, a method for refining a feedstock includes: providing a liquid feedstock to an inner volume of a reactor; flowing a radicalized process gas from a radical generator into the inner volume of the reactor and into contact with the feedstock via a gas diffuser to fractionate the feedstock and to produce one or more fractions of product in a vaporous mixture; and collecting a desired product from the vaporous mixture.

Other and further embodiments of the present disclosure are described below.

BRIEF DESCRIPTION OF THE DRAWINGS

Embodiments of the present disclosure, briefly summarized above and discussed in greater detail below, can be understood by reference to the illustrative embodiments of the invention substantially as depicted and/or described in the appended drawings and as set forth more completely in the claims. Various advantages and features of the present invention will be more fully understood from the following description and drawings. It is to be noted, however, that the appended drawings illustrate only typical embodiments of this disclosure and are therefore not to be considered limiting of its scope, for the disclosure may admit to other equally effective embodiments.

Figure 1:
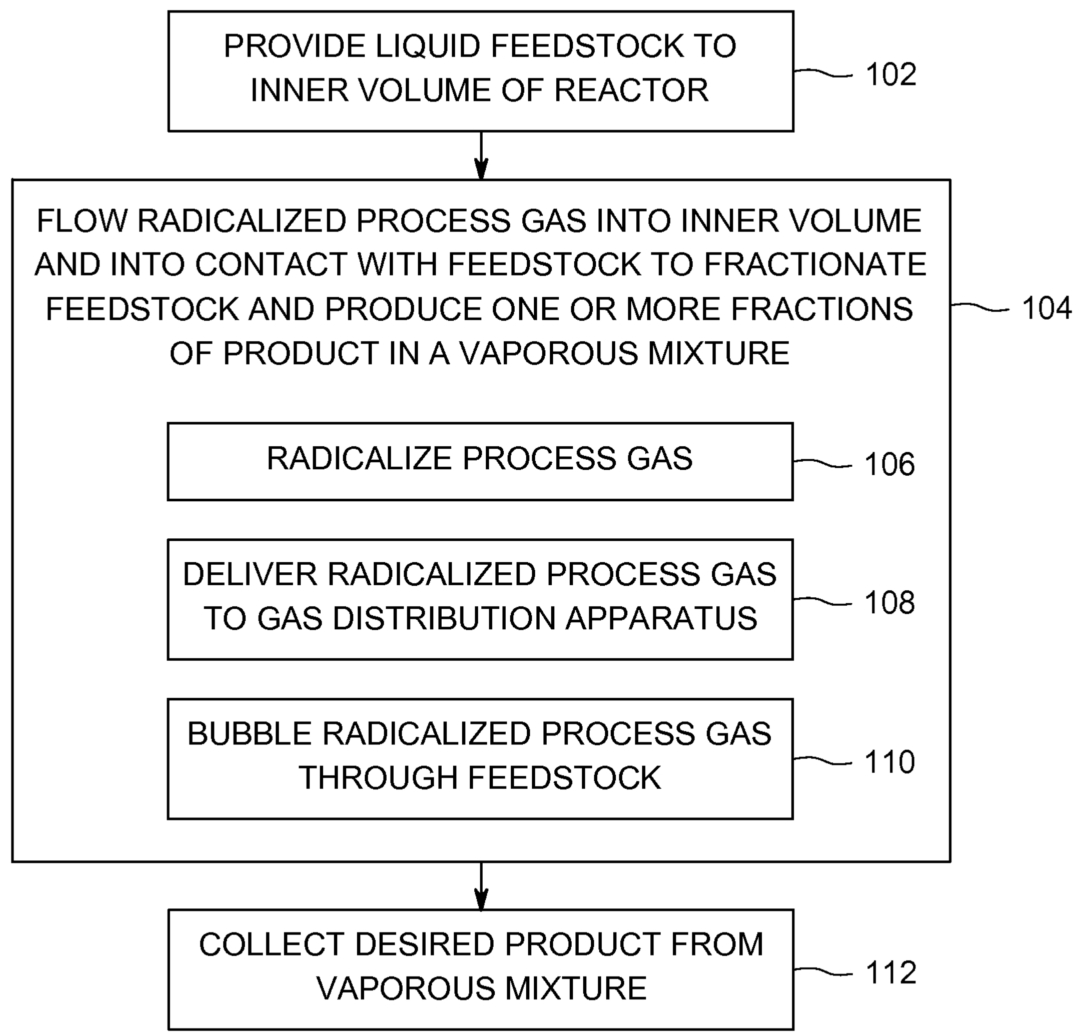
FIG. 1 depicts a process flow diagram of a process for refining a feedstock as described in at least one embodiment, according to the invention, herein.

To facilitate understanding, identical reference numerals have been used, where possible, to designate identical elements that are common to the figures. The figures are not drawn to scale and may be simplified for clarity. It is contemplated that elements and features of one embodiment may be beneficially incorporated in other embodiments without further recitation.

DETAILED DESCRIPTION

Embodiments of the present disclosure provide apparatus and methods for refining crude oils and other oil-based feedstocks. Embodiments of the present invention may advantageously refine oils and other feedstocks more efficiently as compared to conventional methods and apparatus, for example, by use of one or more of low temperature, low pressure, or catalyst-free conditions. Embodiments of the present invention also provide a modular reactor that can advantageously rapidly scale up or scale down production as desired.

FIG. 1 depicts a process flow diagram of a method 100 for refining a feedstock to produce one or more desired product in accordance with embodiments of the present invention. The method 100 may be carried out in any suitable apparatus capable of control in accordance with the teachings provided herein and, moreover, may be a batch process or a continuous process. Illustrative, but non-limiting, examples of embodiments of a suitable apparatus according to the invention are described below with respect to FIGS. 2-4. Exemplary, but non-limiting, desired products obtained by refining crude oil feedstock include cetane (for diesel components) and decane (for gasoline components) using the method 100, for example in refining systems described with respect to FIGS. 2-5, below.

The method 100 starts at 102 where a feedstock is provided to an inner volume of a suitable reactor, such as the reactor described below with respect to FIGS. 2-4. The feedstock may be one or more of crude oil, synthetic or the like. The feedstock is typically maintained at about no more than 60 percent of the volume of the reactor, or in some embodiments not more than about 50 percent of the reactor volume, or in some embodiments between about 30 to about 60 percent of the reactor volume. In some embodiments, a level sensor may be provided to determine the liquid level, such as one or more of a high level sensor, a low level sensor, or the like. Alternatively, the feedstock may be provided for a period of time at a known flow rate to fill the reactor to a desired level.

The reactor may be maintained at a relatively low pressure, such as less than about 5 atmospheres, for example about 1 to about 4 atmospheres, or in some embodiments about 1 to 2 atmospheres. The low pressure advantageously allows for the use of more inexpensive equipment as compared to typical refining equipment, which operate at about 10 to about 50 atmospheres.

The feedstock may be maintained at a temperature that is low enough (at the given pressure) to maintain the feedstock in a mostly liquid state and to prevent and/or minimize the vaporization of components from the feedstock and their escape in unreacted form from the reactor. For example, in some embodiments, a temperature inside the reactor may be maintained at about 100 to about 300 degrees Celsius. In some embodiments, for example when the feedstock is crude oil, the temperature inside the chamber of the reactor may be maintained at about 150 to about 200 degrees Celsius. Other temperatures may also be used, depending upon the feedstock, desired output, acceptable yield and purity of the output, or the like, although the feedstock needs to be at least at its boiling temperature. The feedstock may be heated in any suitable manner, such as by one or more of preheating the feedstock prior to delivery to the reactor (e.g., heating delivery conduits or staging vessels), heating the feedstock within the reactor (e.g., providing a heat jacket or other energy source outside the reactor or providing a heat source within the reactor), heating a process gas provided to the reactor, or the like.

At 104, a radicalized process gas is flowed into the inner volume of the reactor and into contact with the feedstock to fractionate the feedstock and to produce one or more fractions of product in a vaporous mixture. The process gas may be any suitable gas or gaseous mixture that when radicalized is a source of an active hydrogen or hydrocarbon species. Examples of suitable process gases include one or more of methane ($CH_4$), gas mixtures containing methane, hydrogen gas ($H_2$), clean natural gas (CNG), ethanes, propanes, butanes, isobutanes, carbon dioxide ($CO_2$), and the like. The process gas may be selected to hydrogenate, methylate, ethylate, etc., and the like, the different reactants and/or components formed following the fractionation of the feedstock, as discussed below to produce desirable refined products.

As indicated, at 106, the process gas is first radicalized to provide the radicals to react with and fractionate the feedstock. The process gas may be radicalized by any suitable means, such as by providing sufficient energy to dissociate the process gas and form radicals. Examples of suitable techniques to radicalize the process gas include exposing the process gas to a RF plasma, a microwave plasma, a hot wire or hot filament at a suitable temperature to dissociate the process gas, or the like.

As noted above, the radicalized gas is brought into contact with the feedstock to break down the feedstock and to react with the feedstock to create desired products in vapor phase mixed with liquid phase droplets of raw or treated feedstock (e.g., a vaporous mixture). The radicalized process gas is flowed into the inner volume of the reactor via a gas distribution apparatus, as indicated at 108. Contacting the feedstock with the radicalized process gas promotes a reaction between the feedstock and the radicalized process gas that fractionates the feedstock and creates a hydrocarbon-based vaporous mixture of products in gaseous phase as well as small liquid phase droplets carried in the vaporous mixture. In at least one embodiment of the invention, the vaporous mixture is advantageously generated without the use of catalysts.

The radicalized gas may be provided at a flow rate to provide a desired concentration of the radicalized gas within the feedstock. For example, in some embodiments, a flow rate of between about 10 to about 100 cubic feet per minute. (CFM) may be provided. The pressure of the radicalized gas upstream of the reactor (for example, flowing from a gas source to the gas distribution apparatus), may be controlled to a level sufficient to prevent backstreaming of feedstock into conduit lines that supply the radicalized gas to the reactor. In some embodiments, the upstream pressure of the radicalized process gas is maintained at about 1 to about 4 atmospheres. Such pressure control may be achieved by control of the flow rate of the process gas. A pressure sensor may be provided in the gas delivery line to monitor the upstream pressure of the process gas.

In some embodiments, as indicated at 110, the radicalized gas may be bubbled through the feedstock to promote dispersion of the radicalized gas within the feedstock (e.g., to increase surface area of contact). For example, the radicalized gas may be provided to a gas inlet within the reactor. The gas inlet may be below the surface of the feedstock within the reactor. In some embodiments, the radicalized gas may be delivered to a gas distribution apparatus, such as a gas diffuser, positioned within the reactor and, in some embodiments, submerged within the feedstock.

In some embodiments, the gas distribution apparatus may be capable of heating the radicalized gas and feedstock. In some embodiments, the gas distribution apparatus is configured to be heated to at least about 300 degrees Celsius (e.g., to heat the radicalized gas and feedstock to a desired temperature, for example, of about 100 to about 300 degrees Celsius). For example, in some embodiments, the gas distribution apparatus is at least partially fabricated from conductive materials and is coupled to a power supply to flow electrical current through the gas distribution apparatus to generate heat.

At 112, desired products are collected from the vaporous mixture. For example, products contained in the vaporous mixture are carried out of the reactor in a gas stream. Different products, having various boiling points, can be independently collected using distillation apparatus to separate desired products based upon their respective boiling points. The vaporous mixture of product may further be fractionated by thermal treatment to further break down or modify the output product as desired and/or to reduce contaminants present in the vaporous mixture. The thermal treatment may be performed within the reactor prior to removing the vaporous mixture for product collection, or downstream of a gas outlet of the reactor. In some embodiments, the thermal treatment is provided by a reformer. The reformer includes one or more wires or filaments coupled to a power supply to heat the one or more wires to a suitable temperature to treat the vaporous mixture passing through the reformer. In some embodiments, the one or more wires may be heated to a temperature of about 100 to about 800 degrees Celsius. The temperature may be selected dependent upon the species desired to be modified. The reformer may be disposed within the inner volume of the reactor or downstream of a gas outlet of the reactor.

Upon completion of collection of the desired products at 112, the method 100 generally ends. However, the method 100 may include variations and/or additional processing techniques. For example, the method 100 may include a plurality of reformers, operating at the same or different conditions (e.g., varying temperatures and/or pressures), to produce various components, which are later collected and separated using distillation apparatus capable of separating refined products of differing boiling points. Moreover, as discussed in greater detail below, the radicalized process gas may be separated, collected, and recycled or delivered to the gas source or the process gas radicalizer for reuse. Reusing reclaimed process gas advantageously facilitates operation of the reactor in a closed-loop system that reduces input requirements.

The method 100 may be a batch process to process a pre-determined amount of feedstock. Alternately, the method 100 may be a continuous process capable of operating indefinitely and automatically. For example, the amount of feedstock within the reactor may be monitored and additional feedstock provided to maintain a desired level of feedstock within the reactor. At least one embodiment includes a sensor to monitor the density of the feedstock at the bottom of the reactor. When a pre-determined density is sensed, a first valve may open, draining the denser feedstock from the bottom of the reactor and signaling a second valve to open, delivering additional feedstock to the reactor until, for example, a desirable density of the feedstock is obtained or a certain height level of feedstock within the chamber of the reactor is reached. Alternatively, the first and second valves may be opened and closed based on the lapse of a pre-determined amount of time. In this manner, a volume of feedstock capable of being refined into a desired product can be maintained. The high density feedstock may be drained from the reactor.

Figure 2:
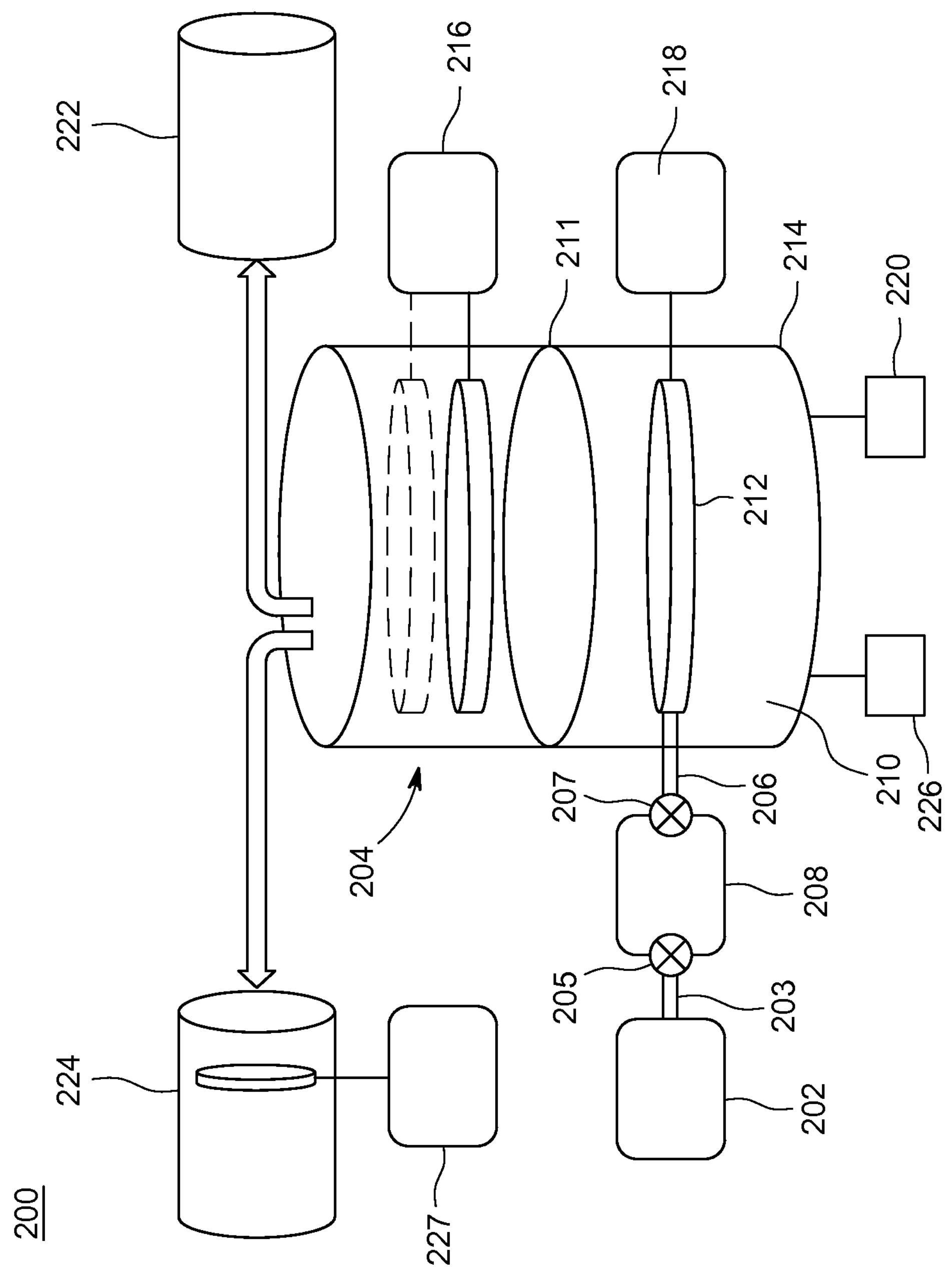
FIG. 2 depicts a refining system comprising a reactor, a radical generator; a gas diffuser; and a reformer for treating a feedstock, as described in at least one embodiment according to the invention, herein.

FIG. 2 depicts a refining system 200 suitable for performing the method 100 described above. The refining system 200 generally includes a reactor 204, a radical generator 208, a gas diffuser 212, and one or more reformers 216. The reactor 204 may include a closed vessel or chamber 214, such as a pressure vessel, having an inner volume to hold a feedstock to be refined, such as any of the feedstock discussed above. For example, the reactor 204 may be a tank fabricated from stainless steel or other suitable materials. A feedstock source 226 may be coupled to the chamber 214 via an inlet to periodically supply feedstock to the chamber 214 during processing. Although depicted at a bottom of the chamber, the inlet to the chamber 214 may be located at any suitable position along the bottom, sides, or top of the chamber 214. For example, the inlet may be positioned to minimize any recombination of the treated feedstock by intermixing with the raw feedstock and/or to minimize quantities of raw feedstock that may exist in sections of process piping that have been isolated and no longer maintain a flow (e.g., dead legs).

The radical generator 208 is coupled to the inner volume of the reactor 204 to provide a radicalized process gas to process the feedstock. A gas source 202, which provides any of the process gases discussed above, is in fluid communication with an inlet 205 of the radical generator 208 via a conduit 203. An outlet 207 of the radical generator 208 is coupled to the inner volume of the reactor via a conduit 206. In use, the radical generator 208 receives the process gas from the gas source 202, radicalizes the process gas, and delivers the radicalized process gas to the inner volume of the reactor 204. The radical generator 208 may comprise at least one of a radio frequency (RF) plasma source, a microwave plasma source, or a thermal radical generator such as a hot wire (or filament) assembly.

The radicalized process gas may be provided to the reactor 204 via a gas inlet. The gas inlet may be an opening or nozzle disposed in a sidewall of the reactor 204 or may be part of a gas distribution apparatus disposed within the reactor 204. For example, in some embodiments, a gas diffuser 212 is disposed within the chamber 214 of the reactor 204 and has the appearance of a typical shower head, although many designs are possible. The gas diffuser 212 may be positioned at a level low enough to be submerged in the feedstock 210. For example, the feedstock 210 may have a fluid level 211 that is, for example, between about 30 to about 60% of the volumetric capacity of the reactor 204 (e.g., of the chamber 214). In at least one exemplary embodiment, the fluid level 211 is about 50% of the volumetric capacity of the chamber 214.

The gas diffuser 212 facilitates distribution (or diffusion) of the radicalized process gas through the feedstock 210. In some embodiments, the gas diffuser 212 contains an inner volume and a plurality of openings coupling the inner volume of the gas diffuser 212 to the inner volume of the reactor 204. In some embodiments, the gas diffuser comprises a perforated conduit that is shaped to supply the radicalized process gas to a larger area. For example, the conduit may be shaped in a spiral pattern. The radicalized process gas is flowed through the openings and bubbled into the feedstock 210, creating a hydrocarbon-based vaporous mixture above the fluid level 211.

In some embodiments, a heater 218 may be provided to heat the feedstock to a desired temperature to enhance to breakdown of the feedstock into the hydrocarbon-based vaporous mixture. The heater 218 may be disposed outside of or inside of the reactor 204 and may be any suitable heater that can provide heat energy to the feedstock in a process compatible manner. For example, in some embodiments, the heater 218 may be coupled to an outer wall of the chamber 214 and may provide heat energy by flowing a heat transfer fluid through the heater, by flowing electrical current through one or more conductive elements of the heater, or the like. Alternatively or in combination, the heater 218 may be disposed inside of the chamber 214 of the reactor 204. Alternatively or in combination, the heater 218 (or another heater) may be configured to heat the radicalized process gas such that the radicalized process gas provides heat energy to the feedstock. For example, in some embodiments, the heater 218 may be coupled to the gas diffuser 212 to heat both the radicalized process gas flowing through the gas diffuser 212 as well as the feedstock in which the gas diffuser 212 is immersed. In some embodiments, the gas diffuser 212 itself may act as the heater by coupling a power source to one or more conductive portions of the gas diffuser 212 (e.g., one or more conductive elements), such as a gas conduit through which the radicalized process gas flows.

At least one reformer 216 is provided within the refining system 200 to further reform the hydrocarbon-based vaporous mixture into desired products. The at least one reformer 216 may be provided within the chamber 214 or downstream of the chamber 214 in a separate vessel. The reformer 216 uses heat energy to break down (or reform) the vaporous mixture into desired products, to remove impurities, or the like. For example, in some embodiments, the reformer 216 includes heated filaments disposed within the chamber 214, as discussed in more detail below with respect to FIG. 5.

The vaporous mixture is flowed out of the chamber 214 from an outlet of the chamber 214 disposed in an upper region above the fluid level 211 of the feedstock 210. The vaporous mixture may then be processed to separate and collect the desired products from the vaporous mixture, for example, based upon the boiling points of the desired products. For example, as shown in FIG. 2, distillation apparatus 222 may be provided to distill the vaporous mixture and obtain the desired products.

The vaporous mixture may also include byproducts, such as contaminants or other refined products that are not desired. Such byproducts may be collected after separation from the desired products, for example, in a second distillation apparatus or as an output from the distillation apparatus 222 (e.g., as discussed below with respect to FIG. 3). In some embodiments, the by-products are collected in a vessel 224. The byproducts may be further refined using a second reformer 227, such as a hydrogenation or de-hydrogenation process. In some embodiments, at least portions of the radicalized process gas may be separated from the vaporous mixture after removing the desired products and collected for reuse, as discussed below.

A drain vessel 220 may be coupled to a bottom portion of the chamber 214 to collect feedstock or other materials drained from the chamber 214. For example, if the density of the feedstock near the bottom of the chamber 214 exceeds a predetermined level, for example as determined by a density sensor or the like, a valve may open to allow the thickened feedstock to drain to the drain vessel 220 for further processing. Additional feedstock may be provided from the feedstock source 226, as discussed above.

Figure 3:
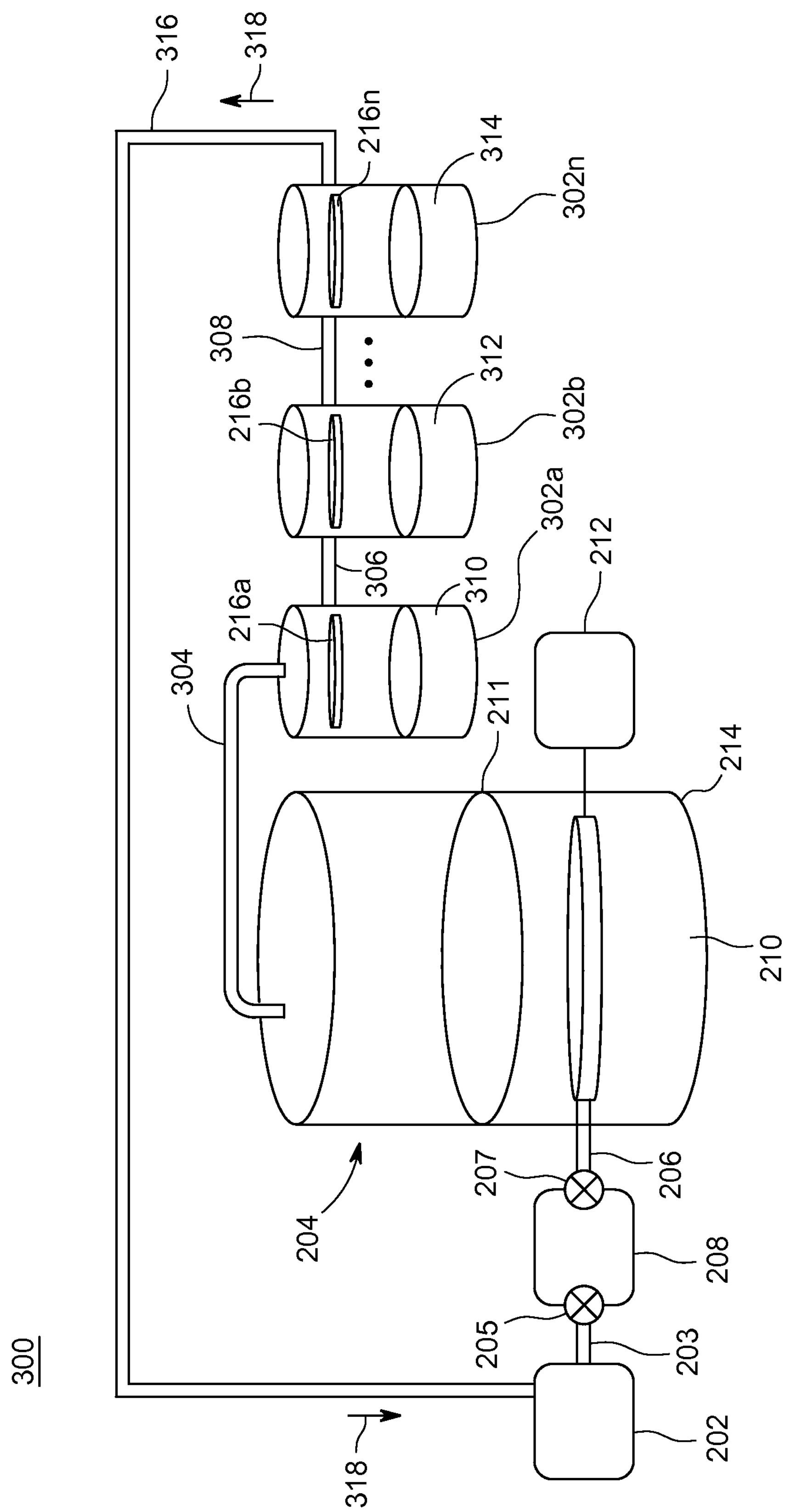
FIG. 3 depicts a second refining system comprising a reactor, a radical generator; a gas diffuser; and a plurality of reformers for treating a feedstock, as described in at least one embodiment according to the invention, herein.

FIG. 3 depicts a second refining system 300 comprising a reactor 204, a radical generator 208; a gas diffuser 212; and a plurality of reformers 216*a*, 216*b* . . . 216*n* for treating a feedstock, as described in at least one embodiment according to the present invention. The second refining system 300 is similar to the refining system 200 described above and similar components are numbered as in FIG. 2. In addition, certain components are excluded for clarity, such as the feedstock source 226 and drain vessel 220. However, components not depicted in FIG. 3 may also be present unless explicitly described otherwise.

The second refining system 300 includes a plurality of fractionator containers 302*a*, 302*b* . . . 302*n*. The plurality of fractionator containers 302*a*, 302*b*, . . . 302*n* are arranged in series such that the first fractionator container 302*a* is coupled to the chamber 214, for example, by a conduit 304, and each successive fractionator container 302*b* . . . 302*n* is coupled to the immediately prior fractionator container 302*a*, 302*b*, etc. (e.g., via conduits 306, 308, etc.) Each fractionator container may further include or be part of distillation apparatus (e.g., a distillation column) to distill a desired product from the vaporous mixture. Thus, the first fractionator container 302*a* may be used to condense and remove a desired product having a highest boiling point, while other products and byproducts having lower boiling points remain in a gas phase in the vaporous mixture and are flowed to the successive fractionator containers (e.g., 302*b*). For example, a first desired product 310 may be condensed into fractionator container 302*a*, a second desired product 312 may be condensed into fractionator container 302*b*, and a third desired product 314 may be condensed into fractionator container 302*n*. In some embodiments, the number of fractionator containers provided in the system may correspond at minimum to the number of desired products to condense from the vaporous mixture. Alternatively or in combination, the various fractionator containers may be used to collect a predetermined quantity of the desired product and the desired product in any given fractionator container may be the same or different from the desired product in any other fractionator container.

In some embodiments, one or more of the fractionator containers (including all) may include a reformers (reformers 216*a*, 216*b*, . . . 216*n* shown in FIG. 3). Each individual reformer 216*a*, 216*b* . . . 216*n*, hydrotreats and/or hydrocracks the hydrocarbon-based vaporous mixture to further tune the quality and/or nature of the products in the vaporous mixture, as discussed above.

In some embodiments, the second refining system 300 further comprises a recycled process gas conduit 316, which allows the process gas to flow to a desired location for collection, recycling, reuse, or the like. For example, the process gas, because it is typically hydrogen, methane, ethane, or the like, has a very low boiling point and is therefore separated at a temperature that is much lower than the temperature to separate refined desired products in containers 302*a-n*. The process gas can then be delivered to the gas source 202 or directly into the radical generator 208 for reuse in the second refining system 300.

Figure 4:
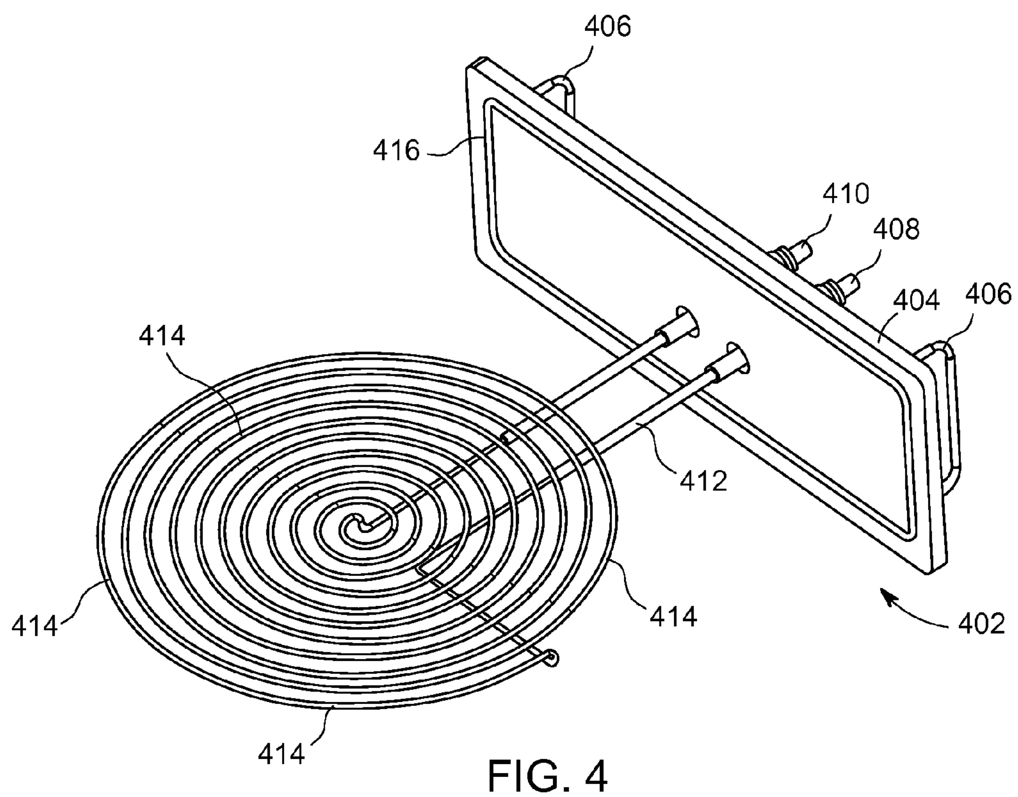
FIG. 4 depicts a perspective view of a gas distribution ring in accordance with some embodiments of the present invention.

FIG. 4 depicts a perspective view of a gas distribution ring 402, suitable for use as the gas diffuser 212 described above with respect to FIGS. 2-3, in accordance with some embodiments of the present invention. The gas distribution ring 402 comprises a conduit 414 supported by a base 404. The conduit 414 is perforated (e.g., contains a plurality of holes) to allow the radicalized process gas to exit the conduit 414. The conduit 414 may be shaped to increase the surface area of the conduit 414 to be disposed within the reactor 204. For example, as depicted in FIG. 4, the conduit 414 may be shaped in a circular spiral pattern, although other patterns and numbers of conduits may be used. In some embodiments, a support 412 may be provided to increase the rigidity of the assembly and reduce any sagging of the conduit 414 with respect to the base 404. The conduit 414 includes a gas inlet port 408 and a gas outlet port 410 to facilitate flowing the radicalized process gas through the conduit 414. The gas inlet and gas outlet ports 408, 410 are located on a side of the base 404 disposed outside of the reactor 204, when installed. The gas outlet port 410 may be plugged such that substantially all radicalized process gases provided to the conduit 414 flow out of the perforations and into contact with the feedstock.

The base 404 may have any suitable shape to support the conduit 414 and to facilitate coupling with the reactor 204. For example, as depicted in FIG. 4, the base 404 may be rectangular, although other shapes may be used. In some embodiments, a groove 416 may be provided to interface with or to contain a sealing element, such as a gasket or an o-ring or the like, to facilitate forming a seal between the base 404 and the reactor 204. In some embodiments, handles 406 may be provided to facilitate handling of the gas distribution ring 402, for example, during installation or removal of the gas distribution ring 402.

In some embodiments, the gas distribution ring 402 may be configured as a heater to heat the radicalized process gas and the feedstock in which the gas distribution ring 402 is immersed. For example, the conduit 414 may be fabricated from a conductive material and the gas inlet port 408 and the outlet port 410 may include or be configured as electrical terminals to supply electrical power to the conduit 414 so that it may be heated by resistive heating. A power source, such as a DC power supply, may be coupled to the terminals (e.g., gas inlet port 408 and gas outlet port 410) to provide power to heat the conduit 414 to a desired temperature.

Figure 5:
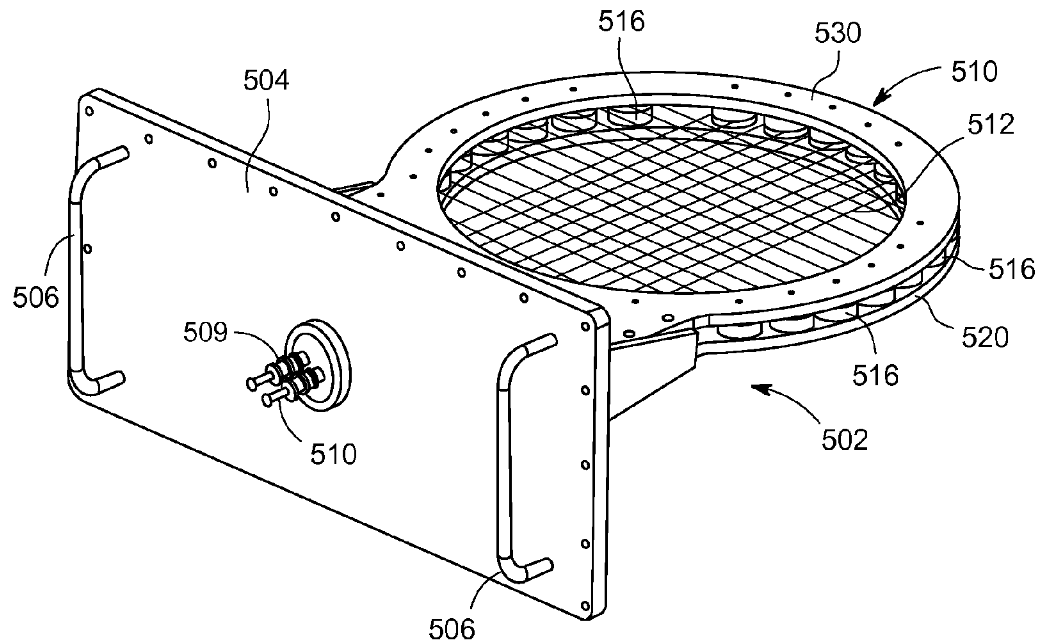
FIG. 5 depicts a perspective view of a reformer having a plurality of filaments in accordance with some embodiments of the present invention.

FIG. 5 depicts a perspective view of a reformer 502 in accordance with embodiments of the present invention and suitable for use as the reformer 216 described above with respect to FIGS. 2 and 3. The reformer 502 includes a base 504 coupled to a frame 510 that supports one or more wires, or filaments 512 strung about the frame 510.

The base 504 may have any suitable shape to support the frame 510 and to facilitate coupling with the reactor 204. For example, as depicted in FIG. 5, the base 504 may be rectangular, although other shapes may be used. In some embodiments, a groove (similar to groove 416 in FIG. 4) may be provided to interface with or to contain a sealing element, such as a gasket or an o-ring or the like, to facilitate forming a seal between the base 504 and the reactor 204. In some embodiments, handles 506 may be provided to facilitate handling of the reformer 502, for example, during installation or removal of the reformer 502.

Electrical power terminals 509 and 510 are disposed on a side of the base 504 outside of the reactor 204 when installed. The electrical power terminals 509, 510 are coupled to the one or more filaments 512 to flow electrical current to heat the filaments 512 during use.

The frame 510 comprises an upper body 530 and a lower body 520. A plurality of vertical supports 516 are disposed between the upper and lower bodies 530, 520 to support the one or more filaments 512 in a desired spacing and pattern. As shown, the one or more filaments 512 are strung in a pattern of first parallel lines in a first direction and second parallel lines in a second direction perpendicular to the first direction. Other patterns may also be used.

Although a few exemplary embodiments of the invention have been described in detail above, those skilled in the art will appreciate that many modifications are possible in embodiments without materially departing from the teachings disclosed herein. For example, a reformer may be housed within a reactor or, alternatively, a reformer may be in located outside the reactor although still in fluid communication therewith. Any and all such modifications are intended to be included within the embodiments of the invention, and other embodiments may be devised without departing from the scope thereof.

The invention claimed is:

1. A reactor for refining a feedstock, comprising:

a chamber having an inner volume to hold a liquid feedstock, a feedstock inlet port, a process gas inlet port, and an outlet port;

a gas diffuser housed within the chamber and coupled to the process gas inlet port;

a radical generator coupled in fluid communication with the inner volume via the gas diffuser, and at least one reformer, wherein the at least one reformer comprises a plurality of filaments configured to be coupled to a power source to heat the plurality of filaments to a desired temperature for thermally treating a vaporous mixture passing through the at least one reformer, wherein the at least one reformer is in fluid communication with the inner volume downstream of the process gas inlet port.

2. The reactor of claim 1, wherein the radical generator is at least one of a radio frequency (RF) plasma source, a microwave plasma source, or a thermal radical generator.

3. The reactor of claim 1, wherein the gas diffuser comprises a hollow distribution ring having a perforated surface.

4. The reactor of claim 1, further comprising a heater to heat feedstock to a desired temperature when disposed within the inner volume.

5. The reactor of claim 4, wherein the gas diffuser comprises one or more conductive elements that form the heater.

6. The reactor of claim 1, wherein the at least one reformer is housed within the chamber.

7. The reactor of claim 1, further comprising a conduit for delivering a recycled process gas from the at least one reformer to at least one of the radical generator, the gas diffuser, or the inner volume of the chamber.

8. The reactor of claim 1, further comprising a plurality of reformers.

9. The reactor of claim 1, wherein the process gas is at least one of hydrogen, methane, ethane, or clean natural gas.

10. The reactor of claim 1, further comprising a controller to control operation of the reactor and configured to communicate with a remote computer network.

11. A reactor for refining a feedstock, comprising:

a chamber having an inner volume to hold a liquid feedstock, a feedstock inlet port, a process gas inlet port, and an outlet port;

a gas distribution ring having a plurality of holes forming a perforated surface within the inner volume;

a radical generator coupled in fluid communication with the inner volume via the gas distribution ring;

a reformer having a plurality of filaments disposed downstream of the gas distribution ring, wherein the reformer is configured to be coupled to a power source to heat the plurality of filaments to a desired temperature to thermally treat a vaporous mixture passing through the at least one reformer during processing; and a controller to control operation of the reactor and configured to communicate with a remote computer network.

* * * * *